(12) United States Patent
Collazo

(10) Patent No.: US 7,695,519 B2
(45) Date of Patent: Apr. 13, 2010

(54) MODULAR TIBIAL BASEPLATE

(75) Inventor: Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 347 days.

(21) Appl. No.: 11/177,087

(22) Filed: Jul. 8, 2005

(65) Prior Publication Data

US 2007/0010890 A1    Jan. 11, 2007

(51) Int. Cl.
*A61F 2/38* (2006.01)
(52) U.S. Cl. .................. 623/20.15; 623/20.34; 623/908
(58) Field of Classification Search ............. 623/20.15, 623/20.32–20.34, 20.14, 20.16
See application file for complete search history.

(56) References Cited

U.S. PATENT DOCUMENTS

| | | | |
|---|---|---|---|
| 4,834,081 A | 5/1989 | Van Zile | |
| 4,923,472 A | 5/1990 | Ugolini | |
| 4,936,847 A | 6/1990 | Manginelli | |
| 4,936,853 A | 6/1990 | Fabian et al. | |
| 4,938,769 A | 7/1990 | Shaw | |
| 4,944,756 A | 7/1990 | Kenna | |
| 4,944,757 A | 7/1990 | Martinez et al. | |
| 5,074,880 A * | 12/1991 | Mansat .................... | 623/20.32 |
| 5,152,796 A | 10/1992 | Slamin | |
| 5,152,797 A | 10/1992 | Luckman et al. | |
| 5,326,359 A | 7/1994 | Oudard | |
| 5,413,605 A | 5/1995 | Ashby et al. | |
| 5,556,433 A | 9/1996 | Gabriel et al. | |
| 5,879,394 A | 3/1999 | Ashby et al. | |
| 5,928,286 A | 7/1999 | Ashby et al. | |
| 6,258,127 B1 | 7/2001 | Schmotzer | |
| 6,299,645 B1 | 10/2001 | Ogden | |
| 6,506,216 B1 | 1/2003 | McCue et al. | |
| 6,620,198 B2 * | 9/2003 | Burstein et al. .......... | 623/20.28 |
| 6,719,800 B2 | 4/2004 | Meyers et al. | |
| 6,866,683 B2 | 3/2005 | Gerbec et al. | |
| 6,887,267 B2 | 5/2005 | Dworschak et al. | |
| 2003/0158606 A1 | 8/2003 | Coon et al. | |
| 2003/0171757 A1 | 9/2003 | Coon et al. | |

(Continued)

FOREIGN PATENT DOCUMENTS

EP    1413264 A2 *   4/2004

*Primary Examiner*—Brian E. Pellegrino
(74) *Attorney, Agent, or Firm*—Lerner, David, Littenberg, Krumholz & Mentlik, LLP

(57) ABSTRACT

A modular keel or stem for use as a tibial implant has a central stem portion including a tongue-like coupling portion for insertion into a grooved portion in a bone contacting portion of a tibial baseplate. The modular keel or stem may also include a pair of anti-rotation fins or ribs which extend medially and posteriorly on the medial side and laterally and posteriorly on the lateral side. Proximal portions of the ribs or fins may engage receptacles in the bone contacting of the tibial baseplate. A locking element is provided for engaging the keel or stem coupling portion and the baseplate after the coupling portion of the keel is inserted into the groove to prevent the disassembly the keel from the baseplate. In one embodiment, the baseplate is capable of being inserted in a direction offset from the anterior-posterior direction, such as a medial-lateral direction, after the keel has been implanted. A polymeric bearing insert is provided for placement onto the baseplate in a standard manner.

14 Claims, 11 Drawing Sheets

U.S. PATENT DOCUMENTS

| | | |
|---|---|---|
| 2003/0204263 A1 | 10/2003 | Justin et al. |
| 2004/0073315 A1 | 4/2004 | Justin et al. |
| 2004/0102852 A1 | 5/2004 | Johnson et al. |
| 2004/0117023 A1 | 6/2004 | Gerbec et al. |
| 2004/0117024 A1 | 6/2004 | Gerbec et al. |
| 2004/0225368 A1 | 11/2004 | Plumet et al. |
| 2005/0102031 A1 | 5/2005 | Leonard |
| 2005/0209702 A1* | 9/2005 | Todd et al. ............... 623/20.33 |
| 2006/0195196 A1* | 8/2006 | Pendleton et al. ........ 623/20.34 |

* cited by examiner

MODULAR TIBIAL BASEPLATE

BACKGROUND OF THE INVENTION

This invention relates to a modular tibial component for use in total knee arthroplasty. More particularly, it relates to a modular tibial component for use in Minimally Invasive Surgery (MIS) wherein all the modular tibial components can be installed through an incision on either the medial side or lateral side or on an anterior-lateral or anterior-medial location on the knee.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

In the past, resurfacing of a knee joint was performed with the implantation of prosthetic femoral and tibial components through an incision extending proximally to distally along the anterior surface of the knee adjacent the lateral or medial sides of the patella. This required a comparatively long incision to be made in order to install the prosthetic femoral and tibial component. Recently, there has been progress towards shortening the incision and moving the incision either medially or laterally from the prior art anterior incision. While direct medial or lateral approaches are possible, it is preferred to have an anterior-medial or anterior-lateral approach.

U.S. Patent Publication No. 2003/0171757 relates to such a minimally invasive total knee arthroplasty method and instrumentation used therefor. In addition, in co-pending U.S. application Ser. No. 10/768,520 assigned to the assignee of the present invention discloses instrumentation for use with such a minimally invasive method.

Incisions size, while of secondary importance to not everting or subluxing the patella, has been reduced and may be in the range of 7-9 cm. Consequently it has been found necessary to utilize femoral and tibial prosthetic implants which are adapted to be inserted through this reduced incision. One way of producing such an implant is to make the typical parts of the implant modular so that they may be inserted into a prepared knee in series. For example, with respect to the tibia, a typical tibial implant includes a stem or a keel, a baseplate and a modular bearing insert typically made of a polymeric material such as ultra-high molecular weight polyethylene. Such a modular tibial component is shown in COPENDING U.S. application Ser. No. 11/133,014 assigned to the Assignee of the present invention.

In the present invention, the stem or keel has been made a separate element from the tibial baseplate which supports the polymeric bearing component. The stem and keel includes a coupling feature in the form of a flanged portion which acts as a tongue for insertion into a grooved receptacle on the inferior surface of the tibial baseplate.

Modular prosthetic knee components are known and are shown in U.S. Pat. No. 5,152,796, U.S. Pat. No. 5,326,359, U.S. Pat. No. 6,258,127, U.S. Pat. No. 6,506,216, and U.S. Pat. No. 5,413,605. These patents relate to methods of attaching modular stems or keels to a femoral or tibial component.

SUMMARY OF THE INVENTION

It is one aspect of the invention to provide a modular tibial component with parts which can be inserted into a prepared proximal tibia in series.

It is yet another aspect of the invention to provide a tibial component having a modular keel or stem which can be coupled to a modular tibial baseplate and locked thereto by a locking element after the tibial baseplate has been inserted in a direction offset from the anterior-posterior direction such as, for example, in the medial to lateral or lateral to medial direction.

It is still a further aspect of the invention to provide a modular polymeric bearing which can be inserted and locked to the tibial baseplate either prior to the operation or intraoperatively.

These and other aspects of the invention are disclosed in a modular tibial implant comprising a tibial baseplate having a medial side, lateral side with a plate having a bone contacting surface and a superior surface extending between the medial and lateral sides of the baseplate. The bone contacting surface of the plate includes an aligned groove or keyway therein which may be oriented in the medial and lateral direction or in a direction offset between the medial or lateral direction and the anterior-posterior direction. Of course the groove on the underside of the plate may be oriented in the anterior-posterior direction.

A modular keel or stem is provided, which keel has a central stem portion including a coupling portion in the form of a tongue-like flange for insertion into the groove in the plate. The modular keel or stem may also include a pair of anti-rotation fins which extend medially-posteriorly on the medial side and laterally-posteriorly on the lateral side of the tibial baseplate. The coupling flange provided on the keel slidably engages the groove in the baseplate. The baseplate is inserted after the keel has been implanted. A locking pin or bolt may be inserted through an aperture in the keel/baseplate to prevent the disassembly thereof. If a threaded locking element is used then the keel or stem aperture may be threaded. The baseplate is capable of being inserted in a medial to lateral or lateral to medial direction after the keel has been implanted. A polymeric bearing insert is provided for placement on the baseplate. Alternately, the polymeric bearing insert could be molded directly onto the baseplate. The coupling flange on the keel or stem could be oriented and the baseplate inserted at about 45° to the medial-lateral direction towards the anterior or even directly anterior depending on where the incision is made in the knee. The keel or stem portion may be in the form of a pegged stem as shown in U.S. Pat. No. 4,938,769 or a straight or an offset stem with or without fins.

On a portion of the keel below the baseplate after assembly, the keel or stem includes a first fin extending radially outwardly from the stem portion at a posterior angle to the medial direction and a second fin extending radially outwardly of the stem at a posterior angle to the lateral direction. In general, the fin preferably extends at about a 30 degree angle from a medial-lateral plane posteriorly on both sides, thus forming a V-shape. Alternately the fins could extend in the medial-lateral direction. The inferior or bone contacting surface of the tibial baseplate may include a pair of inferiorly extending ribs for aligning with proximal end portions of each of the first and second fins. The proximal surfaces of the fins help transfer proximal-distal loads from the baseplate to the keel or stem.

The preferred polymeric insert has an inferior surface which engages the superior surface of the baseplate. The polymeric insert may have an aperture therethrough for receiving the locking element which is inserted through the baseplate into the stem or keel. The bearing may be placed on the baseplate prior to its being slid onto the keel and then the baseplate/bearing being locked onto the keel by the locking element. Alternately the locking element may be inserted through the baseplate into the keel prior to the bearing being placed on the baseplate. The insert, if not premolded, is locked into the baseplate in any manner well known in the art.

The modular tibial implant is preferably assembled in-situ. Initially the proximal tibia is prepared by resecting the tibia in a standard manner to form a planar surface. A keel receiving recess is then formed in the proximal tibia using a tibial punch system which includes cutting surfaces for providing slots for receiving the fins of the keel or stem. This technique is currently performed when implanting non-modular tibial baseplates having integral keels or stems. In the present method the modular keel or stem element is introduced into the prepared tibia and impacted until its proximal coupling surface is approximately 8 mm above the resected plane of the proximal tibia. As discussed the flanged coupling element on the keel may be oriented in any angular orientation preferably from directly medial-lateral to anterior-posterior. The baseplate has a grooved receptacle similarly oriented so that the baseplate may be slid onto the mating flange to complete a snug tongue-in-groove connection. This results in the baseplate having a standard orientation on top of the proximal tibia. The assembly screw or bolt is then inserted through an aperture in the baseplate into a threaded bore in the keel or stem and tightened to a specific torque requirement. If a baseplate having a pre-molded or inserted polymeric bearing component is utilized, then the screw may be inserted through an island between the medial and lateral condylar surfaces or through aperture in both the polymeric insert and the baseplate into the threaded bore of the keel or stem.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

Figure 1:
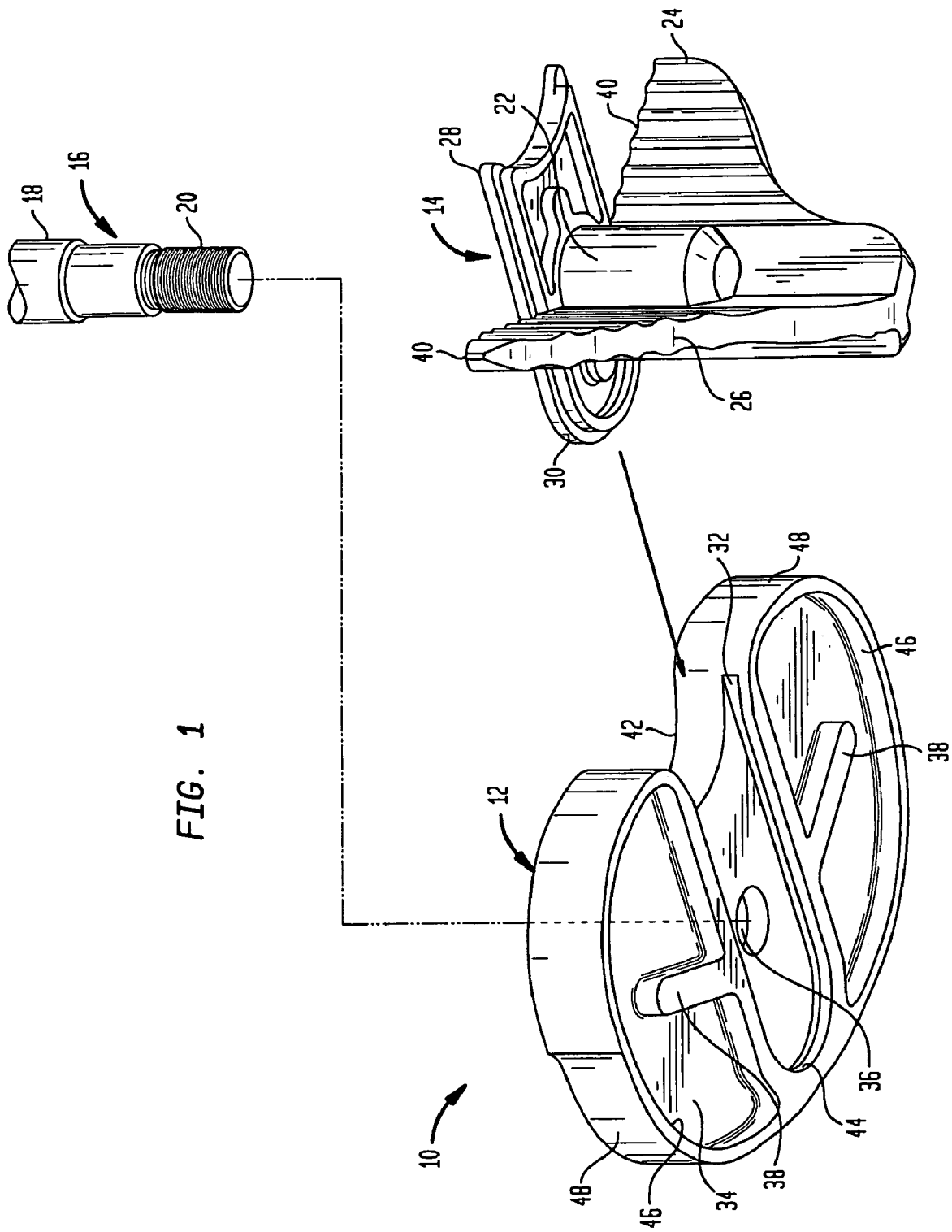
FIG. 1 is an exploded perspective view of the modular tibial keel, baseplate and locking element of the present invention.

Referring to FIG. 1 there is shown a perspective exploded view of the tibial implant of the present invention generally denoted as 10 including a tibial baseplate 12 a modular keel or stem 14 and a locking element 16 preferably in the form of a threaded bolt or screw. Bolt or screw 16 includes a head portion 18 and a threaded portion 20 for engaging a complementary thread in enlarged portion 22 of keel or stem 14.

Keel or stem 14, in the preferred embodiment, includes a pair of fins 24 and 26 which extend at a posterior angle with respect to a medial-lateral plane through the keel or stem 14 after implantation. Keel or stem 14 also includes a flange coupling portion 28. Coupling portion 28 preferably is a planar flat plate having a ledge or tongue portion 30 for slidable engagement in a groove 32 formed on the inferior surface 34 of baseplate 12. In a preferred embodiment groove 32 extends in a generally U-shape around a central portion of the inferior surface 34. Baseplate 12 includes an aperture 36 for receiving locking element 16. The inferior surface of baseplate 12 also includes support elements 38 which are designed to contact superiorly facing portions 40 of fins 24 and 26.

In the preferred embodiment the U-shaped groove portion 32 on the inferior surface 34 of baseplate 12 is in the form of an L-shaped rail which is open to the posterior side of baseplate 12 at 42. In the preferred embodiment U-shaped groove 32 is closed at end 44. In the preferred embodiment the inferior surface 34 of baseplate 12 is recessed thereby forming an outer peripheral wall 46 around the periphery of the baseplate side wall 48.

Figure 2:
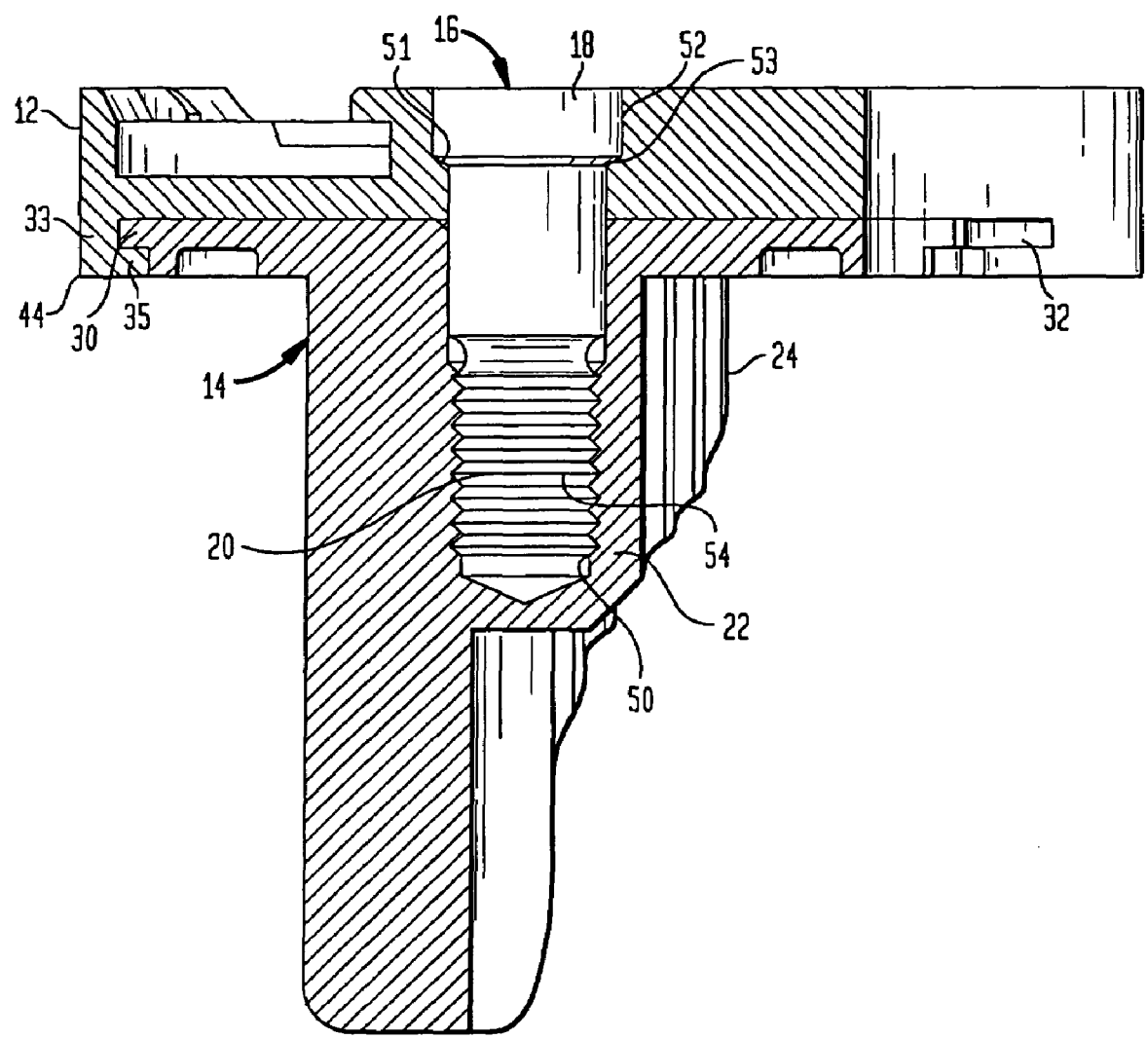
FIG. 2 is a cross-sectional view of the assembled tibial implant of FIG. 1 along an anterior-posterior center line thereof.

Referring to FIG. 2 there is shown a cross-sectional view of the assembled tibial implant shown in FIG. 1. Baseplate 12 is shown assembled to keel or stem 14 and locked thereto by a threaded locking element 16. Locking element 16 is located within a threaded bore 50 formed in enlarged portion 22 of stem or keel 14. Also shown is groove 32 adjacent open end 42 of baseplate 12. On the opposite of side of FIG. 2 is end 44 of the generally U-shaped groove portion 32 in which tongue or ledge 30 has been slidably inserted. Groove 32 is formed by an L-shaped rail having a first leg 33 and a second leg 35 which extends under tongue or ledge 30. It can be seen that baseplate 12 is countersunk at 52 to accommodate head 18 of locking element 16. Preferably, head 18 has a beveled portion 51 adapted to seat on a beveled portion 53 at the bottom of countersunk hole 52. The engagement of threads 20 of locking element 16 and threads 54 of bore 50, when properly torqued, provide a tight connection between the baseplate 12 and keel or stem 14.

Figure 3:
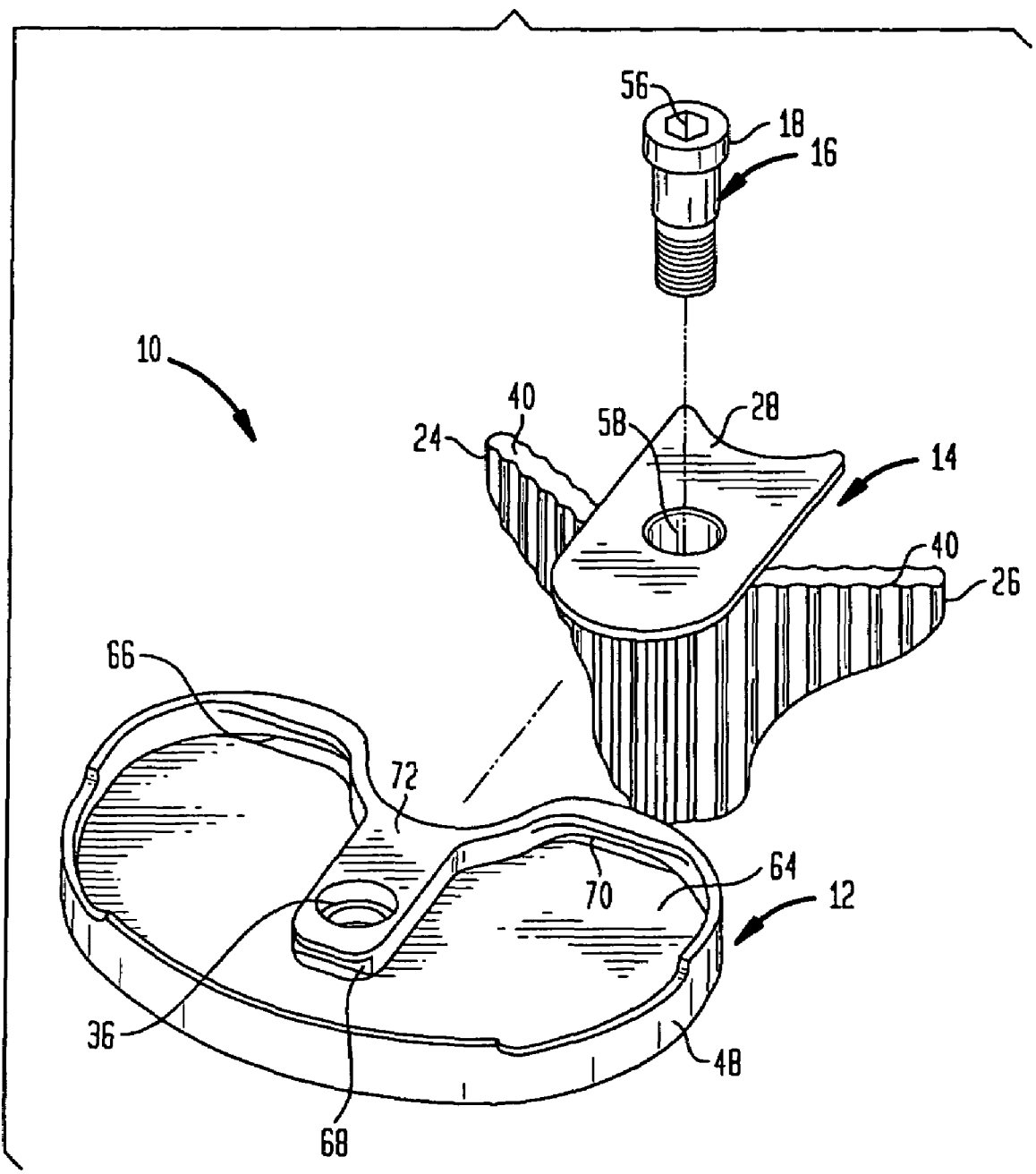
FIG. 3 is a top exploded perspective view of the tibial keel, baseplate and locking element of FIG. 1.

Referring to FIG. 3 there is shown a top perspective view of the unassembled modular tibial implant 10 including baseplate 12, keel or stem 14, and locking element or threaded bolt 16. In this top view it can be seen that head 18 of locking element 16 includes a drive socket 56 which is preferably of a hexagonal shape for receiving an Allen wrench. The locking element 16 is adapted to be inserted into a bore 58 in a center area flange coupling element 28 once the baseplate 12 has been assembled thereto. Also shown are preferably flat top portions 40 of fins 24 and 26 respectively. With respect to baseplate 12 there is shown the superior surface 64 which supports a polymeric tibial bearing element (not shown). Baseplate 12 includes standard locking features such as recesses 66 and 70 for receiving complementary locking features on the polymeric bearing element. Also shown is a central island 72 which separates the left and right condylar bearing portions of the polymeric insert and on which is located aperture 36 which aligns with bore 58 to receive locking element 16 to complete the assembled tibial tray 10. Island 72 can include a recess 68 for receiving a gripping instrument for coupling to the baseplate 12. It can be seen that flanged coupling element 28, in the preferred embodiment, is a planar flat plate having the L-shaped tongues or ledge 30 therearound which acts as a tongue to engage the groove 32 in the tibial baseplate 12. The tongue and groove could also have a dovetail shape for sliding engagement.

Figure 4:
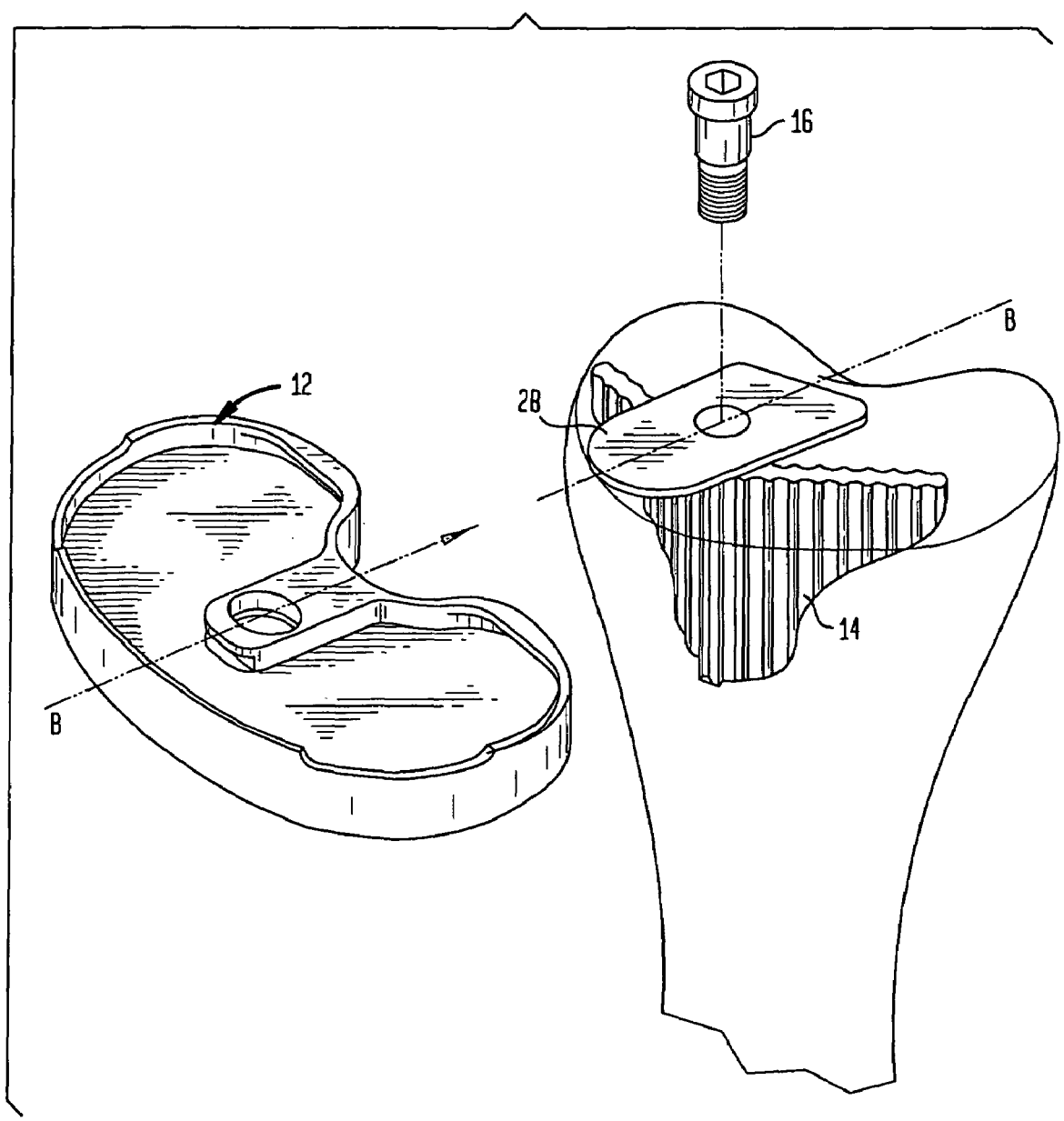
FIG. 4 is an exploded perspective view of the baseplate, keel and locking element of FIG. 1 with the keel shown in place on a proximal tibia with the flange portion of the keel or stem oriented in an anterior-posterior direction.

Referring to FIG. 4 there is shown the keel or stem 14 implanted in the tibia and ready to receive baseplate 12 by moving baseplate 12 generally in a direction from anterior to posterior as shown by axis B.

Figure 5:
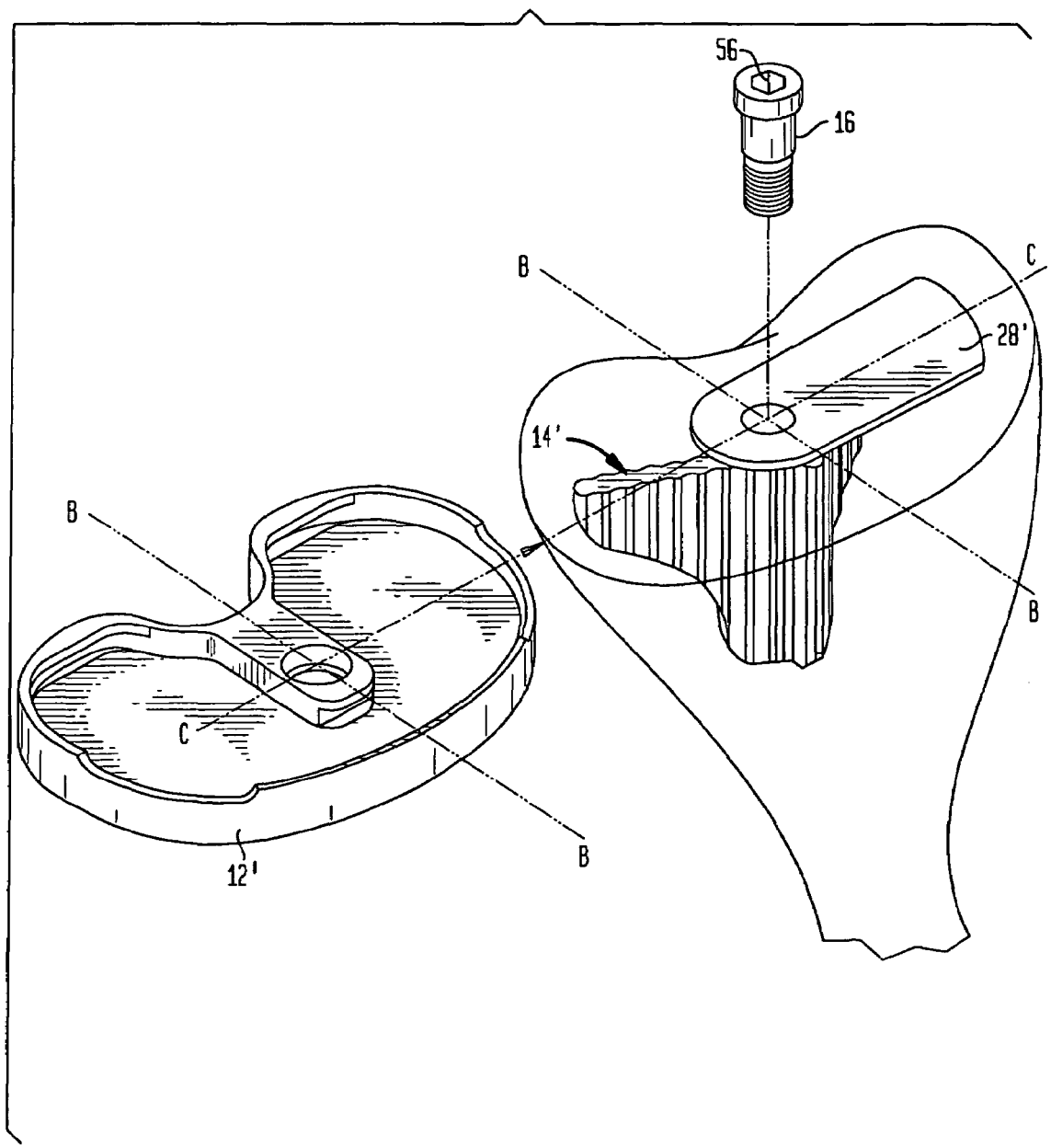
FIG. 5 is the exploded view of FIG. 4 with the flange of the keel or stem oriented in a medial-lateral direction.

Referring to FIG. 5 there is shown a tibial keel 14' implanted within the proximal tibia. Stem or keel 14' includes a flanged coupling element 28' oriented with its long axis C in the medial-lateral direction. Likewise, the U-shape grooved portion 32 on the inferior surface of baseplate 12' is oriented in the medial-lateral direction C so that the baseplate may be slid onto flanged coupling element 28' in the medial to lateral or lateral to medial direction.

Figure 6:
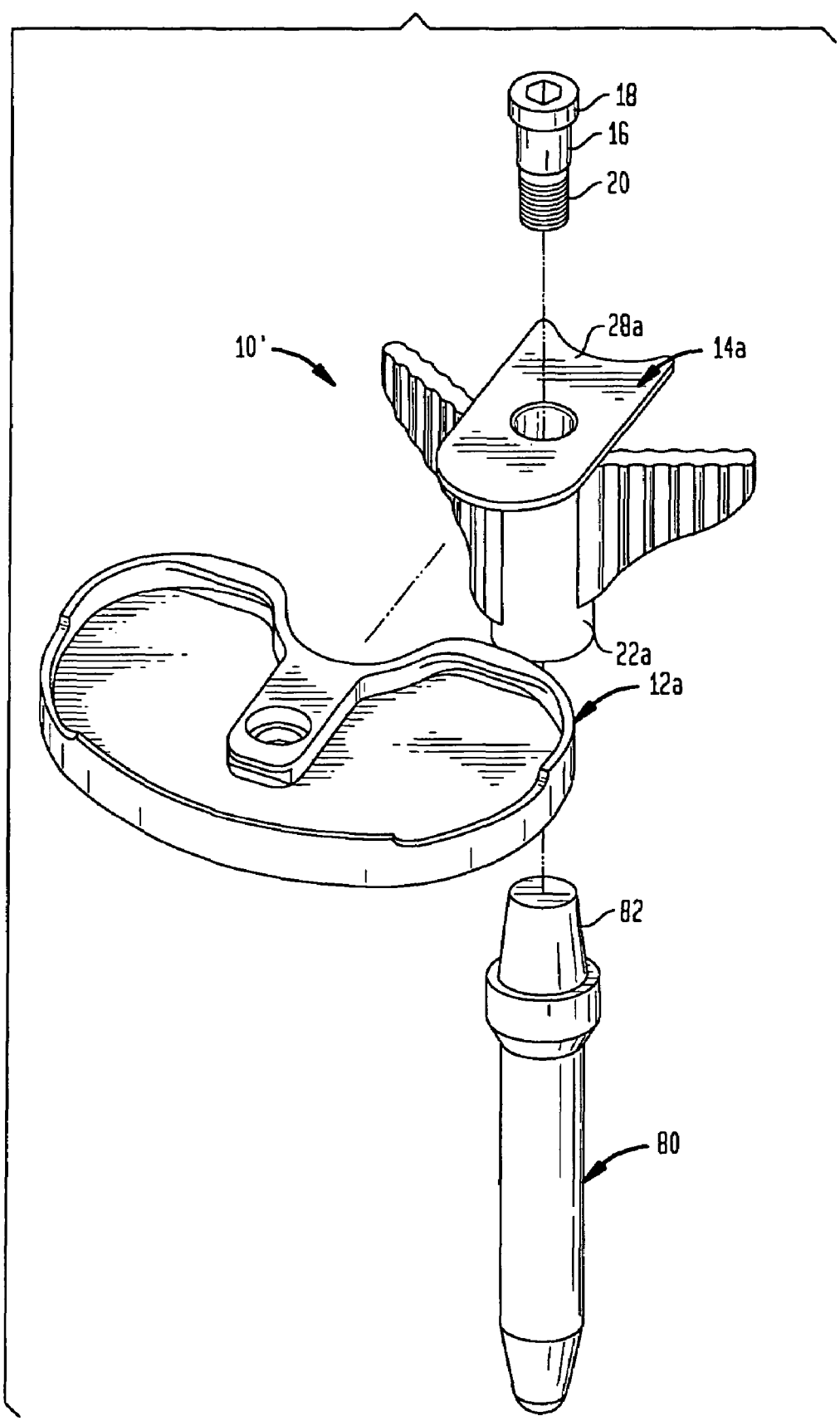
FIG. 6 is the modular tibial implant as shown in FIG. 1 with an additional stem portion adapted to be inserted into a bore in the distal end of the keel or stem element.

Referring to FIG. 6 there is shown modular tibial implant 10' which includes the three basic pieces, baseplate 12a, stem or keel 14a, and locking element 16, and in addition, a modular stem 80. Modular stem 80 has a proximal head portion 82 which may be either cylindrical or, as shown, tapered with a Morse type taper, adapted to be received within a complementary female opening or conical bore within enlarged portion 22a of keel 14a. In this embodiment the head 82 of stem element 80 may be threaded bore to receive the threaded portion 20 of locking element 16 such that the forces holding the modular tibial implant 10' are developed between the head 82 and the head 18 of locking element 16 acting on the bottom surface 53 of countersink 52 in baseplate island 72. These forces insure the tapered connection between the head 82 and a complementary tapered female bore in enlarged portion 22a in keel or stem 14a. Alternately, if head 82 is cylindrical a threaded bore therein insures the tight locking of the modular tibial implant assembly.

Figure 7:
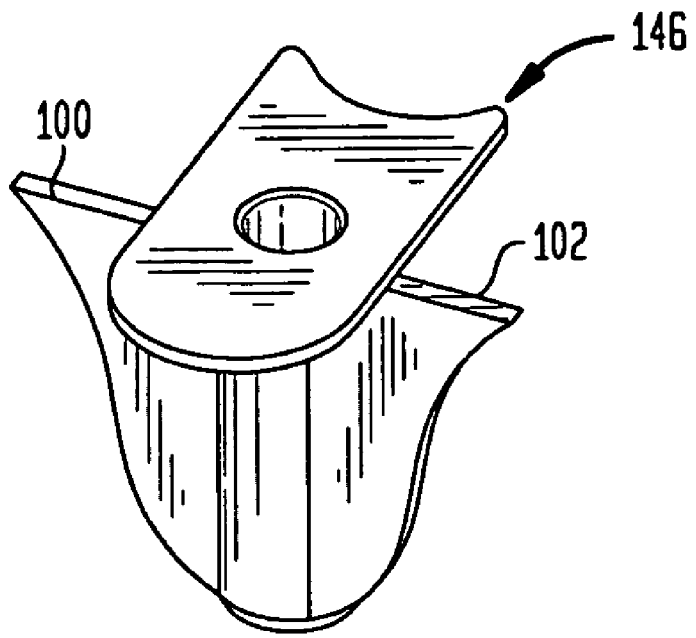
FIG. 7 is a perspective view of a cruciform type keel for an alternate tibial implant.

Referring to FIG. 7 there is shown a cruciform type keel 14b in which a pair of fins 100 and 102 extend in a direction parallel to the medial-lateral plane and a pair of fins 104 extend anteriorly and posteriorly (i.e.—generally perpendicular to fins 100 and 102. Note the posterior fin is not shown in FIG. 7.

Figure 8:
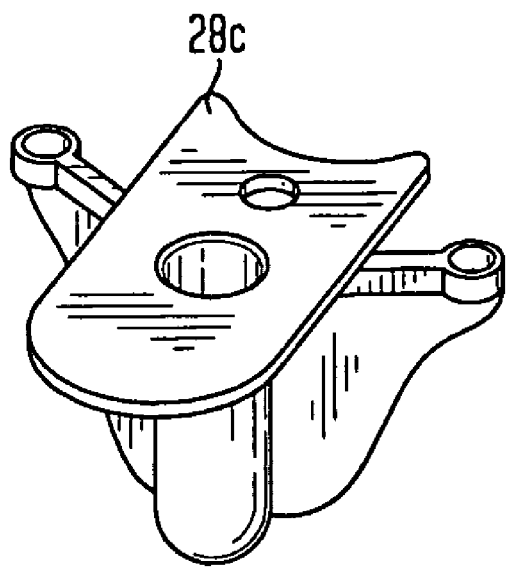
FIG. 8 is a perspective view of the alternate keel with screw eyelets for allowing bone screws to be inserted into the bone surrounding the modular keel.

Referring to FIG. 8 there is shown an alternate keel 14c in which the fins 106, 108 include threaded holes 110 for receiving a bone screw which helps fix the keel to the proximal tibia.

In addition, the flange portion 28c includes a bore 112 for receiving a bone screw for engaging the bone of the proximal tibia.

Figure 9:
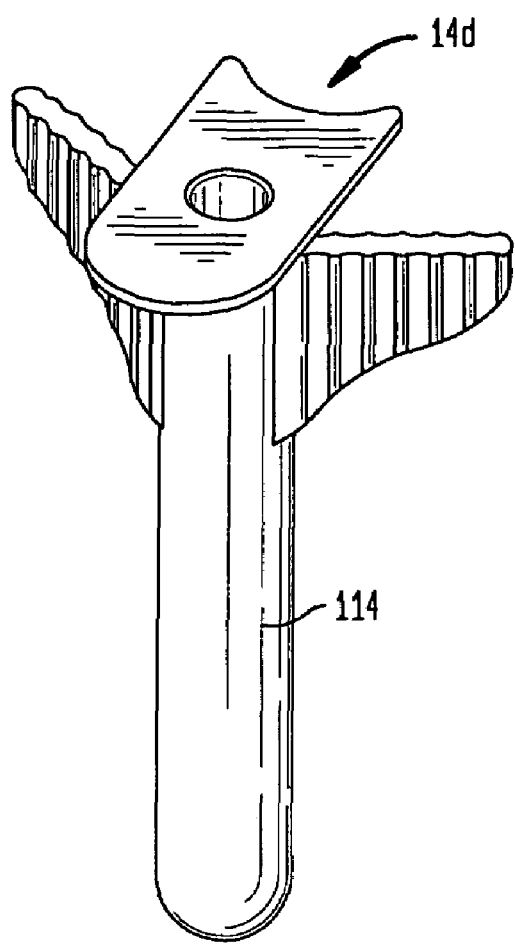
FIG. 9 shows yet another alternate modular tibial keel or stem design having a long stem and a pair of short fins.

Referring to FIG. 9 there is shown an alternate keel design 14d which includes an integral long stem 114.

Figure 10:
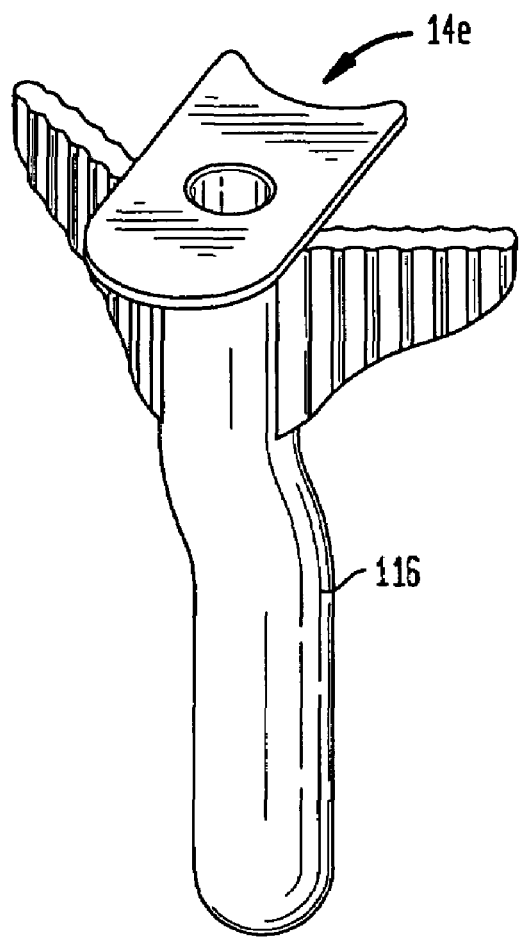
FIG. 10 is the alternate modular tibial keel or stem of FIG. 10 with an offset long stem.

Referring to FIG. 10 there is shown an alternate keel or stem design 14e which includes an offset long stem 116.

Figure 11:
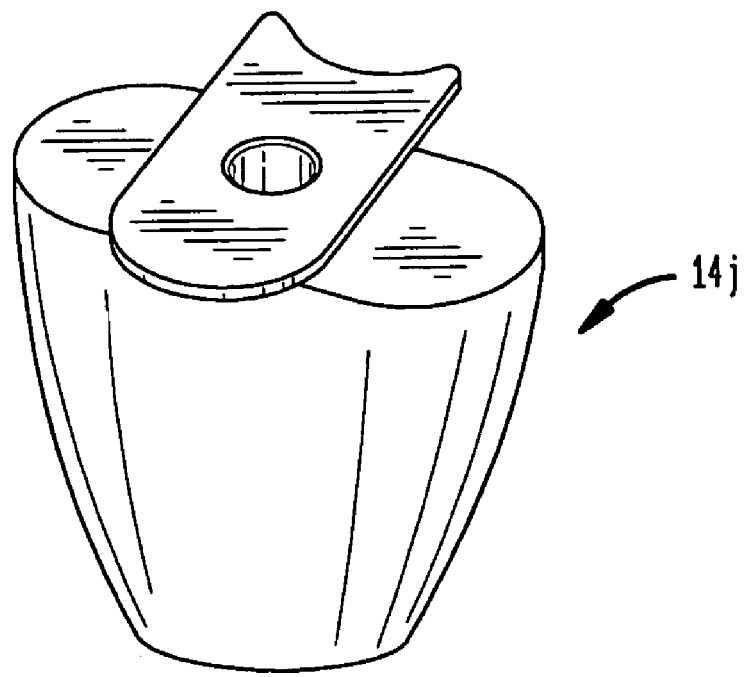
FIG. 11 is a tibial keel or stem in the form of a metaphyseal cone for implantation in the proximal tibia.
Figure 12:
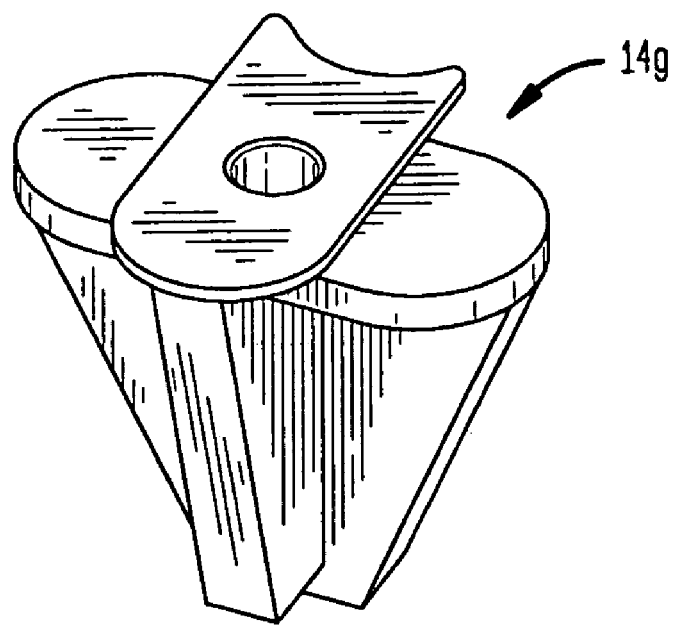
FIG. 12 is a cruciform shaped metaphyseal cone for implantation in the proximal tibia.

Referring to FIGS. 11 and 12 there is shown a proximal tibial metaphyseal implant 14f which may be placed in the proximal tibia after the removal of cancellous bone. Likewise, FIG. 12 shows a cruciform type proximal metaphyseal implant 14g for implantation in a proximal tibia which has been prepared with a cross shaped recess therein.

Figure 13:
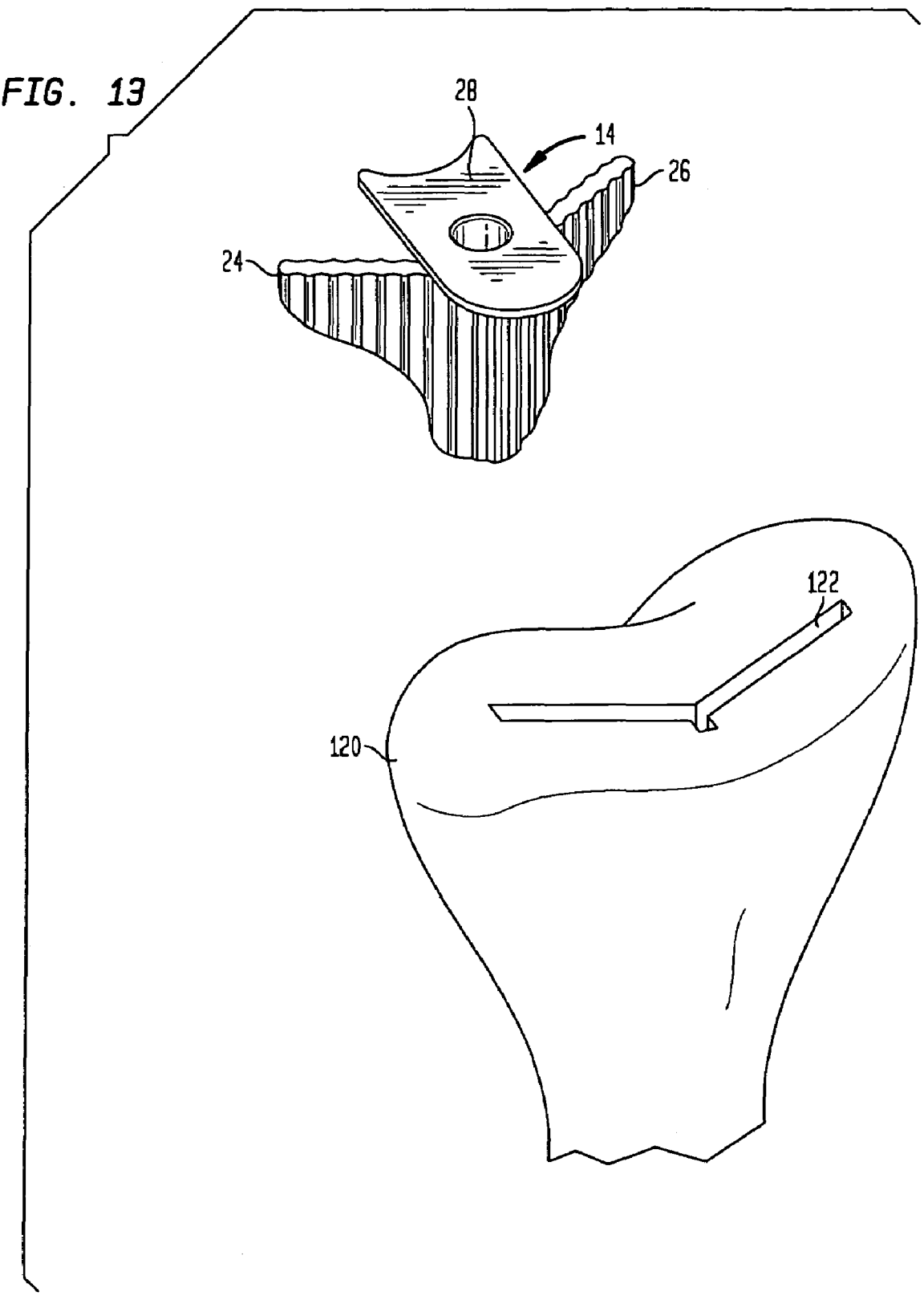
FIG. 13 is a view of the proximal tibia with a receptacle formed therein for receiving the modular tibial keel of the present invention.
Figure 14:
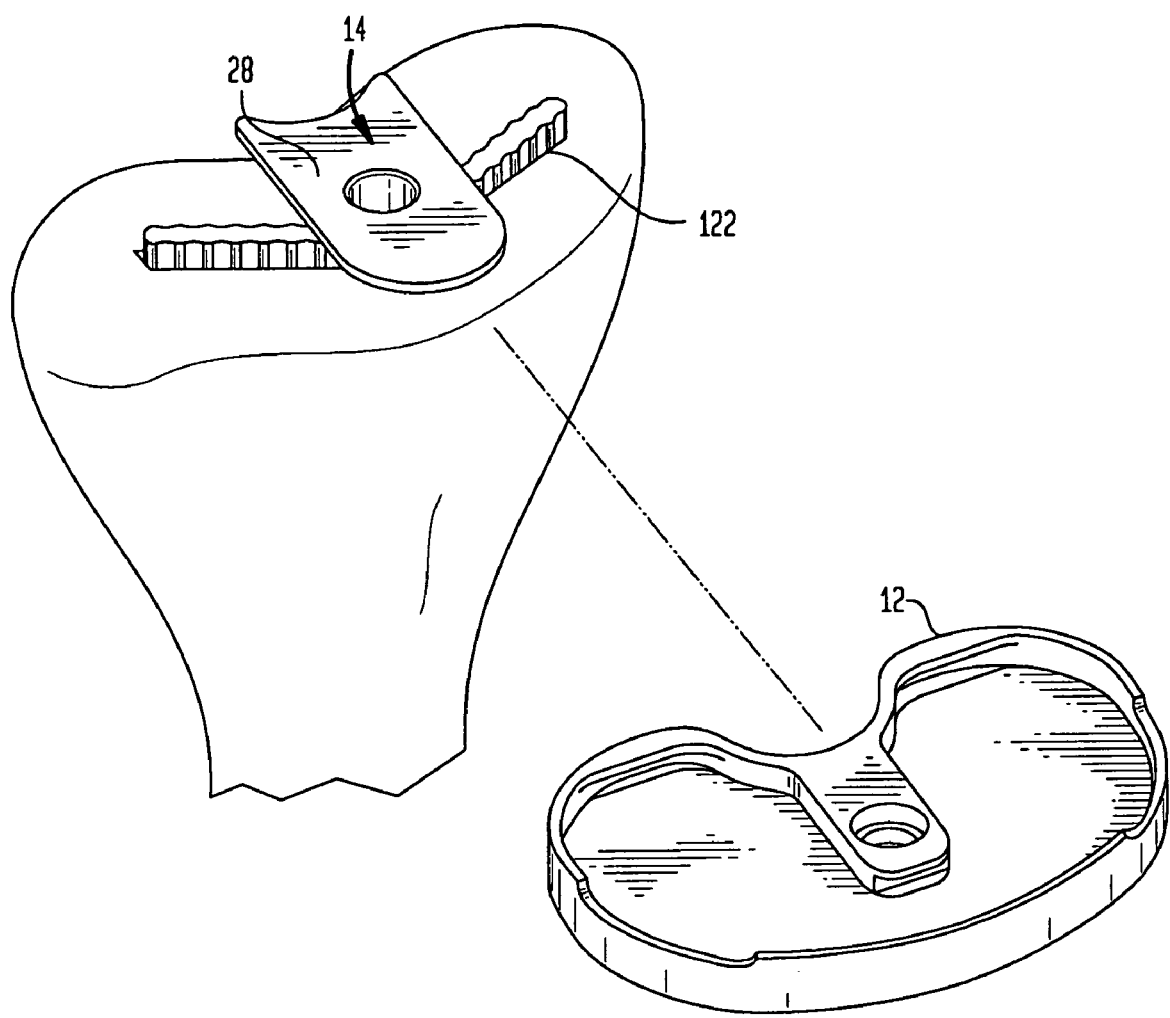
FIG. 14 is a view of the proximal tibia with the modular tibial keel partially implanted in the receptacle formed therein just prior to the assembly of the tibial baseplate thereon.

Referring to FIGS. 13 and 14 there is shown a keel 14 placed above a proximal tibia 120 in which a receptacle or slot 122 has been formed to receive the fins 24 and 26 of keel or stem 14. Recess 122 can be formed by a tibial punch as shown in FIG. 18 of U.S. Pat. No. 6,063,091. FIG. 14 shows keel or stem 14 inserted within the slot 122 with the flange 28 spaced about 8 mm from the prepared planar surface of the tibia with tray 12 spaced anteriorly therefrom ready to be slid onto flange 28. The grooved slot 32 on the bone contacting side of baseplate 12 is then aligned with the tongue of flange 28 and the parts slid together to form a tongue and groove. Once baseplate or tray 12 is placed on flange 28 of keel or stem 14 locking element 16 is inserted therethrough to lock the assembly together. Preferably, a polymeric bearing inset has been preassembled onto the baseplate 12 or, alternately, inserted within the joint space and locked onto baseplate 12 after it has been assembled to stem or keel 14.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A modular tibial implant comprising:
   a polymeric bearing component having an inferior surface,
   a tibial baseplate having a superior surface for receiving the inferior surface of the polymeric bearing component and having a medial side, a lateral side an anterior side and a posterior side with a plate having a distally facing bone contacting surface, the superior surface extending between said sides of said baseplate, said plate including an opening therein, said bone contacting surface having a distally facing portion having a u-shaped receptacle therein open to only one side of said baseplate said receptacle located intermediate the bone contacting surface and the superior surface of the baseplate and the opening open to the bone contacting surface, the receptacle having a u-shaped groove formed on an inwardly facing peripheral surface thereof;
   a modular bone engagement element having a distal bone engaging portion and a u-shaped flanged proximal coupling portion for slidable insertion into said receptacle in a direction generally parallel to said bone contacting surface, the flanged coupling portion having a u-shaped tongue extending around an outer periphery thereof for being received within the groove of the u-shaped receptacle;
   a locking element for engaging said flanged proximal coupling portion of said bone engagement element after the bone engaging element has been slidably inserted into said receptacle to prevent disassembly thereof from said baseplate, wherein said receptacle includes a pair of spaced rails forming grooves for receiving edges of said flanged proximal coupling portion and said modular bone engagement element is a keel or a stem, said keel includes a first fin extending radially outwardly from said stem portion at an angle to said medial side of said baseplate and a second fin extending radially outwardly of said stem at an angle to said lateral side of said baseplate wherein said baseplate bone contacting surfaces includes a pair of inferiorly extending ribs for engaging a proximal end portion of each of said first and second fins.

2. The modular tibial implant as set forth in claim 1 wherein said flanged proximal coupling portion on said keel or stem is a flat plate having tongue portions for sliding in said grooves.

3. The modular tibial implant as set forth in claim 2 wherein said receptacle is generally U-shaped in a plane parallel to a plane of said flat plate.

4. The modular tibial implant as set forth in claim 1 wherein said locking element is a threaded bolt and said keel or stem has a threaded bore therein.

5. The modular tibial implant as set forth in claim 1 wherein said grooves are formed by being spaced dovetail shaped or L-shaped rails.

6. The modular tibial implant as set forth in claim 1 wherein said flanged proximal coupling portion has a longitudinal axis offset from an anterior-posterior direction.

7. A modular tibial implant comprising:
a tibial baseplate having an aperture therein and a bone contacting surface, the baseplate having a groove spaced superiorly from the bone contacting surface and forming an opening open to the bone contacting surface extending outwardly in parallel to the bone contacting surface, said groove being in the form of an L-shaped rail having a first end open to a periphery of the baseplate and a second end closed to the periphery of the base plate;
a modular bone engaging element having a distal stem portion at a first end and a planar flange portion at a proximal second end, said flange portion having a rectangular tongue slidable into said first open end of said L-shaped rail forming the groove of said baseplate; and
means for coupling said bone engaging element to said baseplate including means for locking said flange within said groove, wherein said bone engaging element includes a first fin extending radially outwardly from said stem portion at an angle to a medial direction and said second fin extending radially outwardly of said stem at an angle to a lateral direction and wherein said baseplate has an inferior surface including a pair of inferiorly extending ribs for engaging an end portion of each of said first and second fins.

8. The modular tibial implant as set forth in claim 7 wherein said locking means is a threaded bolt insertable into said baseplate aperture and receivable in a threaded bore in said modular bone engaging element.

9. The modular tibial implant as set forth in claim 7 wherein said groove has first and second facing L-shaped rail portions joined at the second end to form a generally U-shaped receptacle in a plane parallel to said planar flange portion of said bone engaging element.

10. The modular tibial implant as set forth in claim 7 further comprising a polymeric insert for placement on said baseplate having a superior bearing surface and an inferior surface for engaging a superior surface of said baseplate and having an aperture for receiving said means for coupling said bone engaging element upon placement of said insert on said baseplate.

11. A method for coupling a bone engaging element to a tibial baseplate during implantation comprising:
resecting the proximal tibia to form a planar surface;
implanting a bone engaging element having a u-shaped flanged proximal coupling element in the resected proximal tibia, the flanged proximal coupling element having a tongue with a rectangular crossection;
thereafter placing a tibial baseplate having a bone contacting surface and a grooved u-shaped receptacle therein spaced superiorly from the bone contacting surface and forming an opening open to the bone contacting surface, the groove in the form of an L-shaped rail for slidably receiving said tongue of the flanged proximal coupling element on said bone engaging element, said baseplate being inserted in a direction generally parallel to said planar surface in a direction offset from an anterior-posterior direction; and
inserting a locking element into engagement with said flanged proximal coupling element to lock said bone engaging element to said baseplate.

12. The method as set forth in claim 11 wherein said baseplate is inserted onto said flanged proximal coupling element in a generally anterior-medial or anterior-lateral direction.

13. The method as set forth in claim 11 wherein said baseplate is inserted into said flanged proximal coupling element in a generally medial-lateral direction.

14. The method as set forth in claim 11 further comprising the step of forming a recessed area in the resected proximal tibia for receiving a stem or keel of said bone engaging element prior to implanting said bone engaging element.

* * * * *